United States Patent
Wooldridge et al.

(10) Patent No.: US 8,859,522 B2
(45) Date of Patent: Oct. 14, 2014

(54) PROCESSES FOR THE PREPARATION OF REGADENOSON AND A NEW CRYSTALLINE FORM THEREOF

(75) Inventors: Luzviminda T. Wooldridge, Brentwood, MO (US); Chun Ma, Ballwin, MO (US); Sourena Nadji, Olivette, MO (US)

(73) Assignee: Reliable Biopharmaceutical Corporation, St. Louis, MO (US)

( * ) Notice: Subject to any disclaimer, the term of this patent is extended or adjusted under 35 U.S.C. 154(b) by 0 days.

(21) Appl. No.: 14/112,173

(22) PCT Filed: Apr. 26, 2012

(86) PCT No.: PCT/US2012/035263
§ 371 (c)(1),
(2), (4) Date: Nov. 1, 2013

(87) PCT Pub. No.: WO2012/149196
PCT Pub. Date: Nov. 1, 2012

(65) Prior Publication Data
US 2014/0045781 A1 Feb. 13, 2014

Related U.S. Application Data

(60) Provisional application No. 61/479,658, filed on Apr. 27, 2011.

(51) Int. Cl.
*C07H 19/16* (2006.01)
*C07H 1/00* (2006.01)
*C07H 19/167* (2006.01)

(52) U.S. Cl.
CPC .............. *C07H 19/16* (2013.01); *C07H 19/167* (2013.01); *C07H 1/00* (2013.01)
USPC .......................................... 514/46; 536/27.61

(58) Field of Classification Search
USPC ........................................ 514/46; 536/27.61
See application file for complete search history.

(56) References Cited

U.S. PATENT DOCUMENTS

| 6,403,567 | B1 | 6/2002 | Zablocki et al. |
| 7,183,264 | B2 | 2/2007 | Zablocki et al. |
| 7,732,595 | B2 | 6/2010 | Zablocki et al. |
| 8,106,183 | B2 | 1/2012 | Zablocki et al. |

OTHER PUBLICATIONS

International Search Report issued in PCT/US2012/035263 on Sep. 25, 2012.

*Primary Examiner* — Kristin Vajda
(74) *Attorney, Agent, or Firm* — Blank Rome LLP (57) ABSTRACT

This disclosure relates to an improved process for the preparation of regadenoson, pharmaceutically acceptable salts thereof, and hydrates thereof, and for the preparation of intermediates useful in the synthesis of regadenoson. The disclosure also relates to a new crystalline form of regadenoson. Processes for the preparation of the crystalline form, compositions containing the crystalline form, and methods of use thereof are also described.

17 Claims, 4 Drawing Sheets

PROCESSES FOR THE PREPARATION OF REGADENOSON AND A NEW CRYSTALLINE FORM THEREOF

This application is the U.S. national phase of International Patent Application No. PCT/US2012/035263, filed Apr. 26, 2012, which claims the benefit of U.S. Provisional Application No. 611479,658, filed Apr. 27, 2011, the entire contents of which are hereby incorporated by reference.

FIELD OF THE INVENTION

The present invention relates to an improved process for the preparation of regadenoson, pharmaceutically acceptable salts thereof, and hydrates thereof, and for the preparation of intermediates useful in the synthesis of regadenoson. The present invention also relates to a new crystalline form of regadenoson. Processes for the preparation of the crystalline form, compositions containing the crystalline form, and methods of use thereof are also described.

BACKGROUND OF THE INVENTION

Regadenoson [(1-{9-[(4S,2R,3R,5R)-3,4-dihydroxy-5-(hydroxymethyl)oxalan-2-yl]-6-aminopurin-2-yl}pyrazol-4-yl)-N-methylcarboxamine] is a selective $A_{2A}$-adenosine receptor agonist that is a coronary vasodilator. It is currently marketed in the form of a monohydrate as a pharmacologic stress agent indicated for radionuclide myocardial perfusion imaging (MPI) in patients unable to undergo adequate exercise stress.

U.S. Pat. No. 8,106,183 describes amorphous regadenoson, and three forms of regadenoson, referred to as Form A (a monohydrate), Form B and Form C.

The synthesis of regadenoson is described, for example, in U.S. Pat. Nos. 6,403,567 and 7,183,264. The syntheses disclosed are multi-step processes that proceed via 2-hydrazinoadenosine, which is prepared from the corresponding iodo-derivative (2-iodoadenosine). Although these methods are suited to small scale syntheses, they are not well suited for large scale syntheses. Moreover, the yields are low and the staining nature of iodine makes the purification of the 2-iodoadenosine intermediate problematic. It is desirable, therefore, to find new methods of synthesis that provide a convenient method for making large quantities of the material in good yield and high purity.

SUMMARY OF THE INVENTION

The present inventors have found that regadenoson, and hydrates thereof (such as regadenoson monohydrate) may be prepared in high purity and high yield in one step using a 2-haloadenosine (e.g., 2-fluoroadenosine) as a starting material. The present inventors surprisingly found that 2-hydrazinoadenosine may be prepared from 2-fluoroadenosine in higher yield and at higher conversion rate than from the corresponding 2-iodo or 2-chloroadenosine derivatives.

In one aspect, the present invention relates to a process for the preparation of regadenoson, derivatives thereof, pharmaceutically acceptable salts thereof, and hydrates thereof, which comprises contacting a 2-haloadenosine with a 4-N-alkylcarboxamide pyrazole (e.g., 4-N-methylcarboxamide pyrazole) or a 4-carboxylate pyrazole in the presence of a metal catalyst and a base.

Thus, in one aspect, the present invention relates to a process for the preparation of a compound of Formula (I), and pharmaceutically acceptable salts thereof, and hydrates thereof:

comprising contacting a compound of Formula (II) with a compound of Formula (III) in the presence of a metal catalyst and a base wherein R is $C_{1-6}$ alkyl (e.g., $C_{1-4}$ alkyl such as methyl, ethyl, isproppyl); and
X is a halogen, such as F, Cl, Br or I.

The compound of Formula (I) may be converted to regadenoson by aminating the carboxylate group of the compound (e.g., by reaction with methylamine)

In a preferred aspect, the present invention relates to a process for the preparation of regadenoson, and hydrates thereof, which comprises contacting 2-fluoroadenosine with 4-N-methylcarboxamide pyrazole in the presence of a metal catalyst and a base.

In another aspect, the present invention relates to a process for the preparation of 2-hydrazinoadenosine comprising contacting 2-fluoroadenosine or 2-bromoadenosine with hydrazine. In a preferred embodiment, 2-fluoroadenosine is reacted with hydrazine. The 2-hydrazinoadenosine may further be converted to regadenoson, or a hydrate thereof.

In yet another aspect, the invention relates to a process for the purification of regadenoson (for example, regadenoson prepared by a method described herein) by subjecting the regadenoson to reverse phase chromatography. The column can be eluted with a water/alcohol (preferably water/methanol).

In yet another aspect, the invention relates to regadenoson having at least 98% purity (e.g., at least 99% or at least 99.5% purity) and comprising 2-fluoroadenosine in an amount up to about 0.2%, based upon the total weight of the regadenoson. The regadenoson may be incorporated into a pharmaceutical composition, such as a parenteral solution.

In yet another aspect, the invention relates to a composition comprising (a) regadenoson, and (b) 2-fluoroadenosine in an amount up to about 0.2%, based upon the total weight of the composition. The composition can be a pharmaceutical composition, such as a parenteral solution.

In yet another aspect, the invention relates to a pharmaceutical composition comprising regadenoson made by a process of the present invention.

The present inventors have also discovered a new crystalline form of regadenoson, referred to herein as Form D. Thus, in a further aspect, the present invention relates to a novel crystalline form of regadenoson. In another aspect, the present invention relates to a process for the preparation of the new crystalline form. In certain embodiments, the new crystalline form may be prepared by a process that does not involve isolating any intermediate regadenoson compound. In additional aspects, the present invention relates to compositions containing the crystalline form, and to methods of use thereof.

DETAILED DESCRIPTION OF THE INVENTION

Improved Processes for the Preparation of Regadenoson and Derivatives Thereof and Hydrates Thereof In one aspect, the present invention relates to a process for the preparation of a compound of Formula (I), and pharmaceutically acceptable salts thereof, and hydrates thereof:

(I)

comprising contacting a compound of Formula (II) with a compound of Formula (III) in the presence of a metal catalyst and a base (II)

(III)

wherein R is $C_{1-6}$ alkyl (e.g., $C_{1-4}$ alkyl such as methyl, ethyl, isopropyl); and
X is a halogen, such as F, Cl, Br or I.

In a preferred embodiment, X is F. In another embodiment, R is methyl.

In one embodiment, the process further comprises converting the compound of formula (I) to a compound of Formula (IV)

(IV)

wherein $R^2$ is $C_{1-6}$ alkyl (e.g., $C_{1-4}$ alkyl such as methyl, ethyl, isopropyl).

For example, the compound of Formula (I) may be converted to a compound of Formula (IV) by reaction with a primary amine, such as a $C_{1-6}$ alkylamine (e.g., methyl amine).

In another aspect, the present invention relates to a process for the preparation of regadenoson of Formula (IA), pharmaceutically acceptable salts thereof, and hydrates thereof:

(IA)

which comprises contacting 2-fluoroadenosine of Formula (IIA) with 4-N-methylcarboxamide pyrazole of Formula (IIIA) in the presence of a metal catalyst and a base.

(IIA)

(IIIA)

In certain embodiments, the reaction is conducted in a polar solvent. For example, the solvent may be an organic solvent that is miscible with DMSO, such as acetonitrile, dimethylsulfoxide, dimethyl formamide, dichloroethane, dichloromethane, methanol, ethanol, and mixtures thereof. In certain embodiments, the reaction is conducted in a mixture (for example a 1:2 mixture) of dimethylsulfoxide and acetonitrile. In some embodiments, the solvent is dimethylsulfoxide containing from about 10% to about 50% acetonitrile, for example, dimethylsulfoxide containing about 25% acetonitrile.

In additional embodiments, the base has a pK of at least 8 (e.g., a pK of from about 9 to about 12). For example, the base may be selected from sodium hydroxide, potassium hydroxide, triethylamine, cyclic amidine bases (such as, e.g., 1,8-diazabicyclo[5.4.0]undec-7-ene (DBU) or 1,4-diazabicyclo[2.2.2]octane (DABCO)) and combinations thereof. In one embodiment, the base is DBU. In another embodiment, the base is DABCO. In certain embodiments, the amount of base is about 3 equivalents, based on the amount of compound of formula (II). In further embodiments, the metal catalyst is a copper catalyst. For example, the metal catalyst is a copper (II) catalyst. In one embodiment, the copper (II) catalyst is chelated to a resin, for example, a resin attached to iminodiacetic acid. In certain embodiments, the amount of catalyst is about 0.1 equivalent, based on the amount of compound of formula (II).

In further embodiments, the reaction is conducted at a temperature of between about 60° C. and about 90° C., for example between about 70° C. and about 85° C., such as at about 80° C.

In additional embodiments, the reaction proceeds for between about 12 and about 24 hours, such as between about 12 and about 18 hours.

In certain embodiments, the regadenoson is in the form of a hydrate, for example a monohydrate.

Figure 1:
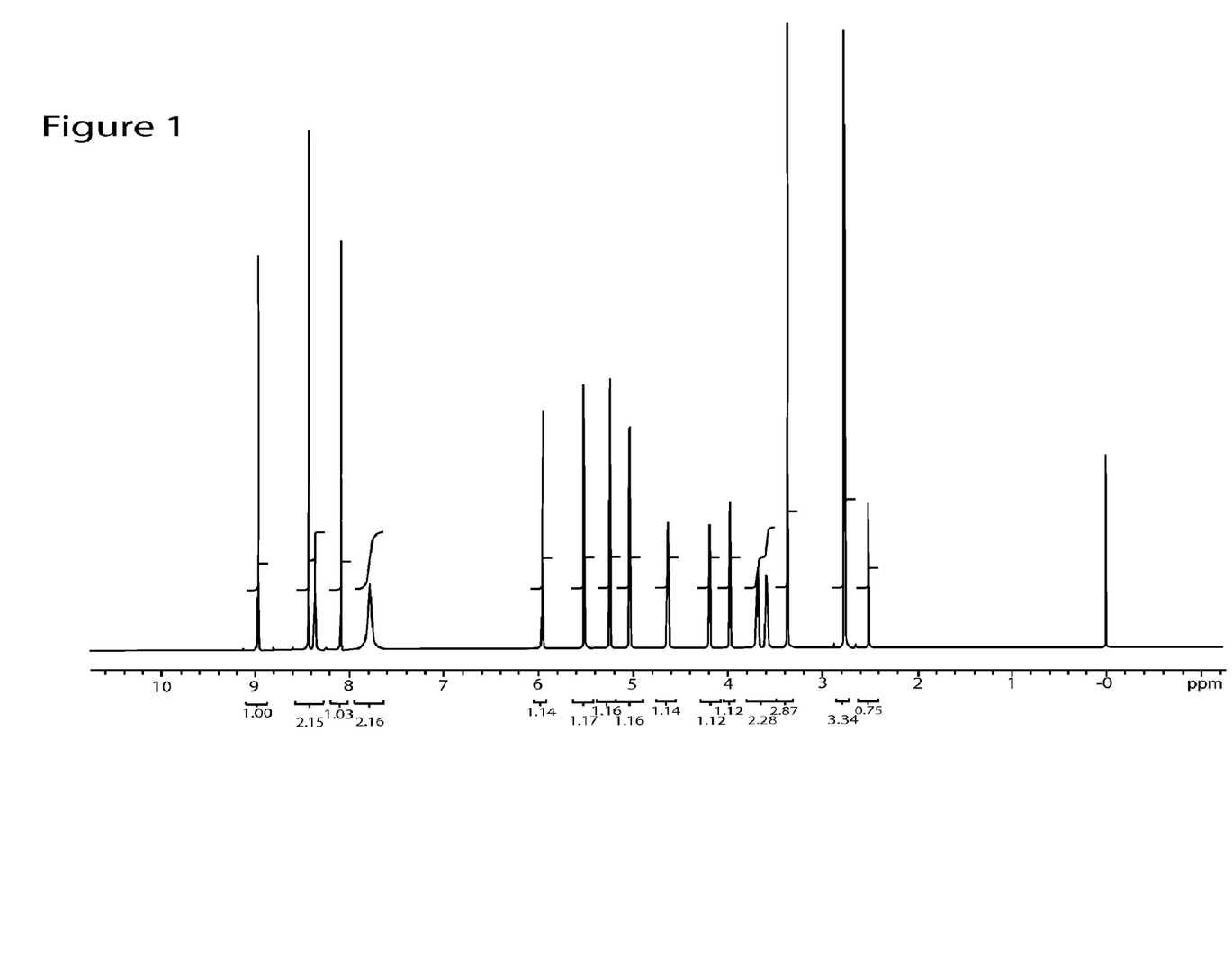
FIG. 1 is a $^1$H nuclear magnetic resonance (NMR) spectrum of regadenoson monohydrate.
Figure 2:
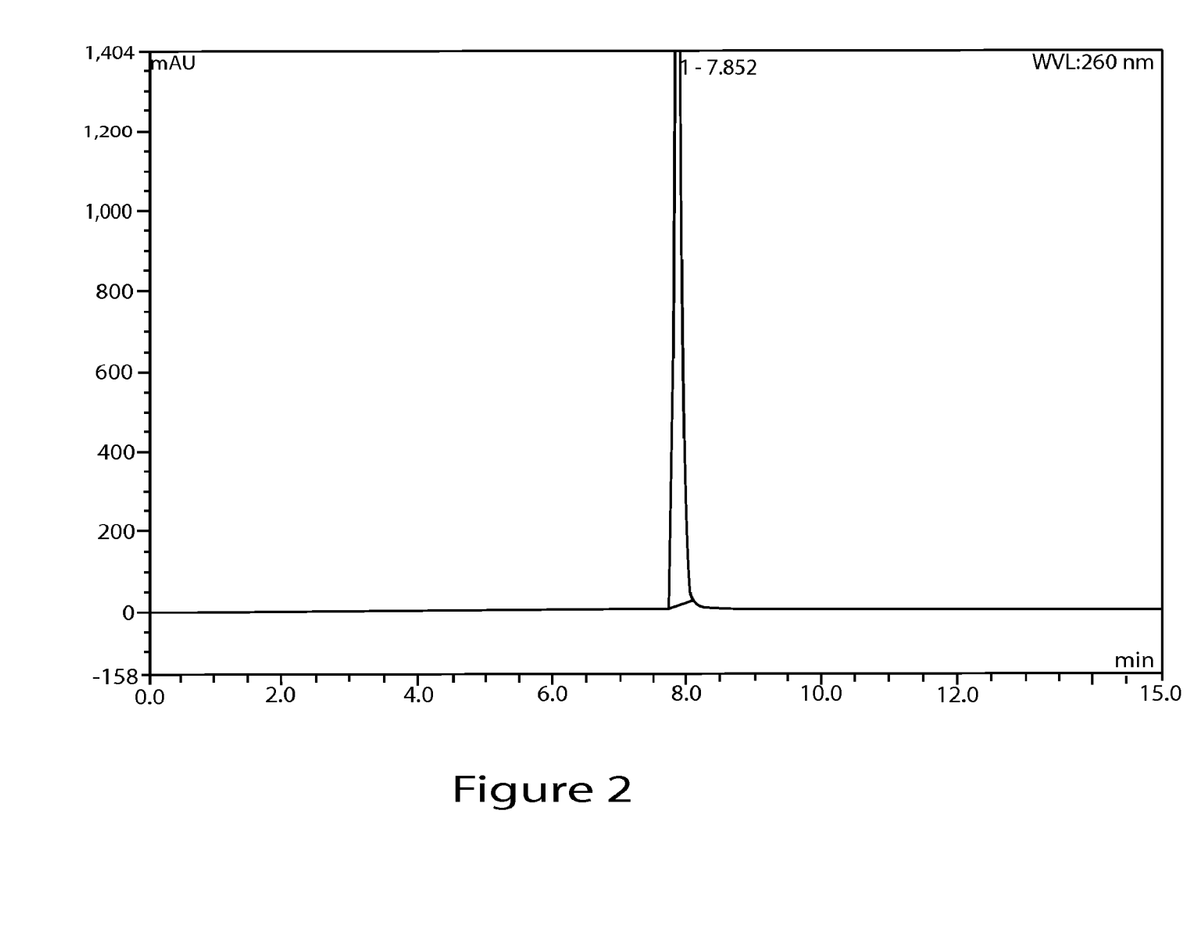
FIG. 2 is a High-Performance Liquid Chromatography (HPLC) trace for regadenoson monohydrate.

FIGS. 1 and 2, respectively, depict the $^1$H NMR spectrum (DMSO-$d_6$) and HPLC trace of regadenoson monohydrate, prepared according to a process of the present invention.

In further embodiments, the regadenoson, pharmaceutically acceptable salt thereof, or hydrate thereof, is greater than about 75% pure, for example, greater than about 80% pure, greater than about 85% pure, greater than about 90% pure, greater than about 95% pure, greater than about 97.5% pure, greater than about 99% pure, greater than about 99.5% pure or greater than about 99.9% pure.

In additional embodiments, the process further comprises converting regadenoson, or a hydrate thereof, to a pharmaceutically acceptable salt thereof. Acid addition salts may be prepared in a standard manner in a suitable solvent from the parent compound and an excess of acid, such as hydrochloric, hydrobromic, sulfuric, phosphoric, acetic, maleic, succinic, methanesulfonic, and the like. Cationic salts may be prepared by reaction with an excess of an alkaline reagent, such as hydroxide, carbonate or alkoxide, containing the appropriate cation. Cations such as $Na^+$, $K^+$ and $Ca^{+2}$ are examples of cations present in pharmaceutically acceptable salts.

In another aspect, the present invention relates to a process for the preparation of 2-hydrazinoadenosine of Formula (V):

(V)

comprising contacting 2-fluoroadenosine or 2-bromoadenosine with hydrazine.

In a preferred embodiment, 2-fluoroadenosine is reacted with hydrazine. In certain embodiments, a molar excess of 2-fluoroadenosine is used. In some embodiments, the molar excess of hydrazine to 2-fluoroadenosine is from about 1.5 to about 20, such as from about 2 to about 12, from about 3 to about 6. In one embodiment, the molar excess of hydrazine to 2-fluoroadenosine is about a 3 molar excess.

In certain embodiments, the reaction is conducted in a polar solvent. For example, the solvent may be an organic solvent that is miscible with DMSO, such as acetonitrile, dimethylsulfoxide, dimethyl formamide, dichloroethane, dichloromethane, methanol, ethanol, and mixtures thereof. For example, in one embodiment, the solvent is dimethylsulfoxide containing from about 10% to about 50% acetonitrile.

In further embodiments, the reaction is conducted at a temperature of between about 60° C. and about 90° C., for example between about 70° C. and about 85° C., such as at about 75° C.

Figure 3:
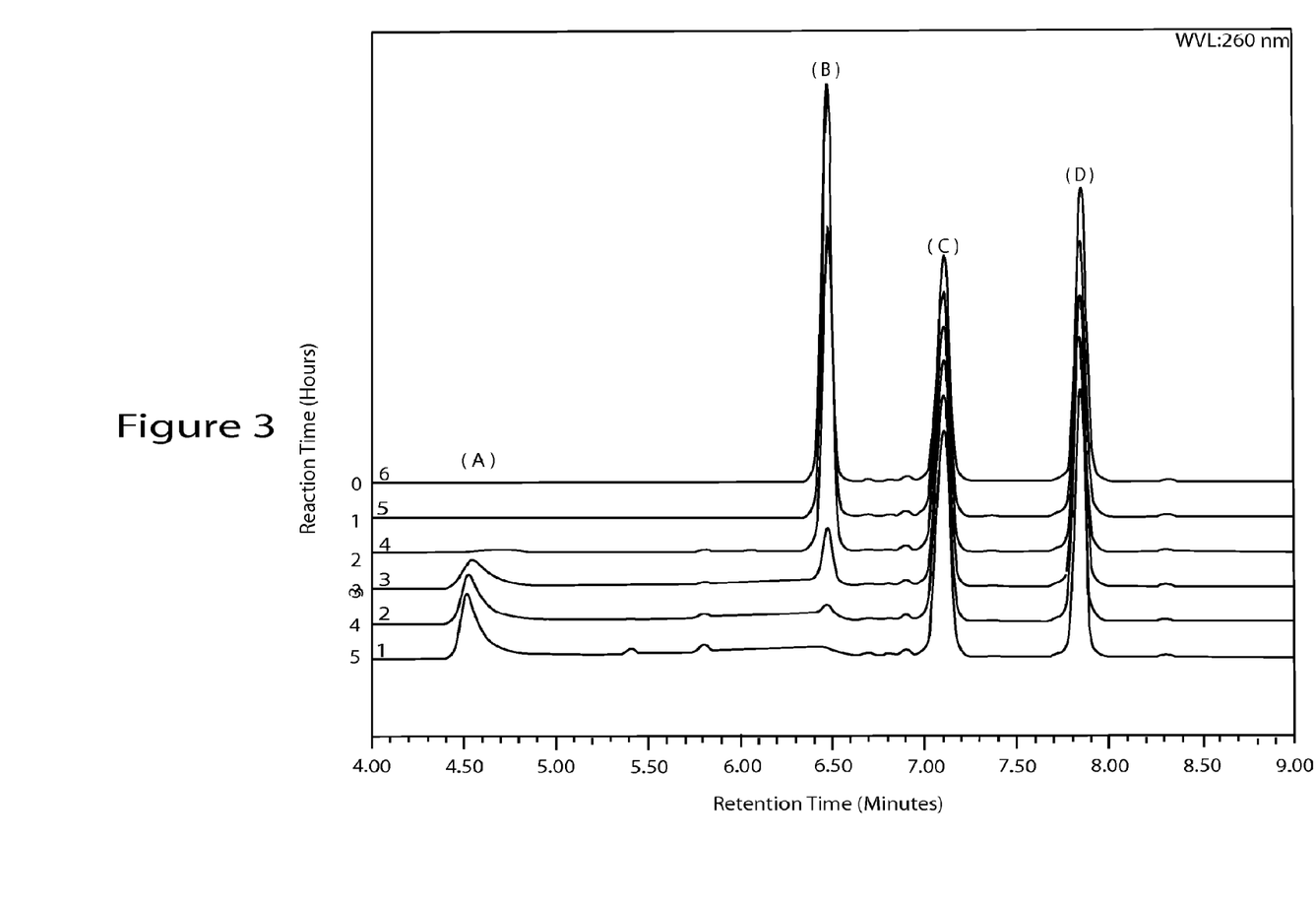
FIG. 3 is an HPLC trace for the formation of 2-hydrazinoadenosine (A) by reaction of hydrazine with a 1:1:1 mixture of 2-fluoroadenosine (B), 2-chloroadenosine (C) and 2-iodoadenosine (D).

FIG. 3 shows a HPLC vs. time trace for reaction of a 1:1:1 mixture of 2-fluoro, 2-chloro- and 2-iodoadenosine with 18 equivalents of hydrazine in dimethylsulfoxide at 75° C. The inventors surprisingly found that the 2-fluoroadenosine was completely converted to 2-hydrazineadeonsine within 5 hours at 75° C. In contrast, the corresponding 2-iodoadensoinse derivative achieved only 50% conversion to 2-hydrazineadeonsine, and the 2-chlorodensoinse achieved only 20% conversion to 2-hydrazineadeonsine under the same reaction conditions.

In certain embodiments, the process further comprises converting 2-hydrazinoadenosine of Formula (V) to regadenoson, or a hydrate thereof.

For example, the 2-hydrazinoadenosine of Formula (V) may be contacted with a compound of formula [R'C(O)CH(CO$_2$R)C(O)R''] to afford a compound of Formula (I):

(I)

in which R is $C_{1-6}$ alkyl and R' and R'' are, independently, hydrogen, $C_{1-6}$ alkyl or aryl, with the proviso that at least one of R' and R'' is hydrogen. In one embodiment, R' and R'' are both hydrogen. The compound of Formula (I) may be further converted to regadenoson. In an exemplary embodiment, the 2-hydrazinoadenosine of Formula (V) may be contacted with ethyl 2-formyl-3-oxopropionate [HC(O)CH(CO₂Et)C(O)H] to afford which may subsequently be converted to regadenoson, or a hydrate thereof, by contacting it with methylamine, according to the procedures outlined, for example, in U.S. Pat. Nos. 6,403,567, 7,183,264 and 7,732,595, as shown below:

Regadenoson can be purified by any method known in the art. Applicants have discovered that one particularly effective method of purification is by subjecting the regadenoson to reverse phase chromatography. The column can be eluted with water/alcohol (preferably water/methanol). For example, the regadenoson can be dissolved in 1:1 mixture of DMSO and methanol, loaded to a reverse phase column, and eluted with water/methanol (gradient with a 5% increase of MeOH). The fractions with the desired HPLC purity, for example, with 99.9% or greater purity, can be combined, filtered and dried (e.g., in a vacuum oven). The reverse phase chromatography can be repeated on fractions have a purity of 99.8% or lower (for example, a purity of between 50% and 99.8%).

Prior to (or alternatively to) performing the reverse phase chromatography, the regadenoson may undergo one or more purification steps, such as (a) filtering, (b) co-evaporation with xylene, and (c) precipitation (for example, from acetonitrile) followed by filtration.

New Crystalline Form of Regadenoson (Form D)

In another aspect, the present invention provides a novel crystalline form of regadenoson which can be identified by one or more analytical methods. Form D is stable under inert conditions. The X-ray powder diffraction (XRPD) pattern of the crystalline form (Form D) is provided in FIG. 4.

Figure 4:
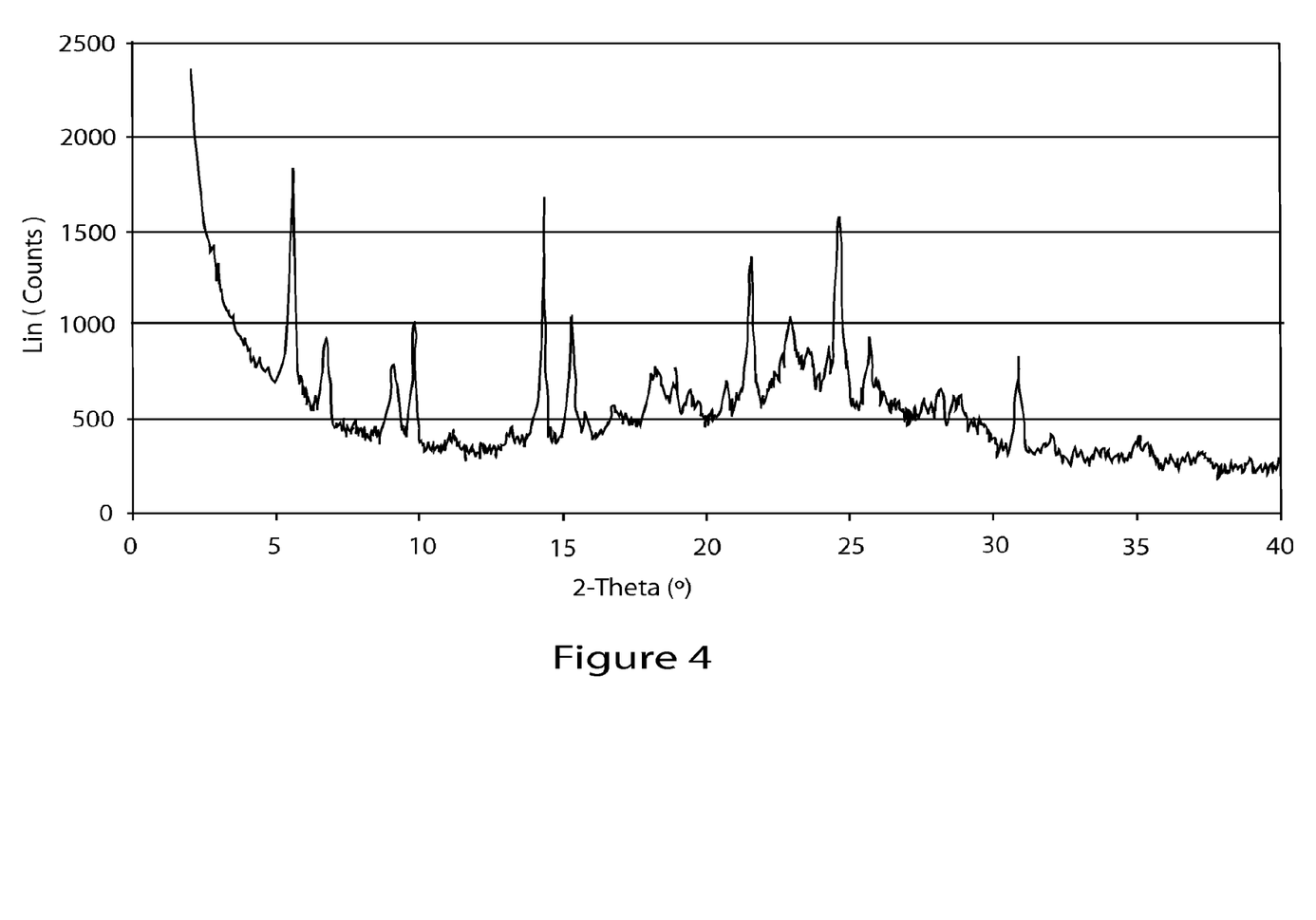
FIG. 4 is an X-ray powder diffraction pattern of Form D of regadenoson.

In a further embodiment, the crystalline form of regadenoson (Form D) is characterized by a X-ray powder diffraction pattern substantially as shown in FIG. 4. With respect to the term "substantially," one skilled in the art would understand that the relative intensities of the peaks can vary, depending upon the sample preparation technique, the sample mounting procedure and the particular instrument employed.

In another embodiment, the crystalline form of regadenoson (Form D) contains between about 0.8 and about 1.7% by weight of water of hydration.

Form D of regadenoson can be in solid form (such as a powder) which is useful for preparing solutions containing regadenoson, such as a parenteral formulation of regadenoson.

In one embodiment, the invention provides a composition comprising Form D of regadenoson. In another embodiment, the invention provides a composition comprising Form D of regadenoson and one or more other solid state forms of regadenoson, such as Form A, B or C of regadenoson.

The crystalline form of regadenoson (Form D) of the invention can be administered alone or as an active ingredient of a formulation. Thus, the present invention also includes pharmaceutical compositions of the crystalline form of regadenoson (Form D) containing, for example, one or more pharmaceutically acceptable carriers.

Compositions

Parenteral solutions may be prepared, for example, by dissolving regadenoson (such as Form D of regadenoson, or regadenoson made by a process of the present invention) in an aqueous solution (such as saline) and optionally adding one or more pharmaceutically acceptable excipients. Thus, in another aspect, the present invention relates to a method of preparing a parenteral solution of regadenoson comprising (i) dissolving (a) Form D of regadenoson, or (b) regadenoson made by a process of the present invention, in an aqueous solution and (ii) optionally adding one or more pharmaceutically acceptable excipients.

Numerous standard references are available that describe procedures for preparing various formulations suitable for administering regadenoson, including Form D of regadenoson and regadenoson made by a process of the present invention. Examples of potential formulations and preparations are contained, for example, in the Handbook of Pharmaceutical Excipients, American Pharmaceutical Association (fifth edition); Pharmaceutical Dosage Forms: Tablets (Lieberman, Lachman and Schwartz, editors) third edition, published by Marcel Dekker, Inc.; as well as Remington's Pharmaceutical Sciences (Arthur Osol, editor), (seventeenth edition).

Administration of the regadenoson (such as Form D of regadenoson) may be accomplished according to patient needs, for example, orally, nasally, parenterally (subcutaneously, intraveneously, intramuscularly, intrasternally and by infusion), by inhalation, rectally, vaginally, topically and by ocular administration.

Various solid oral dosage forms can be used for administering the regadenoson (such as Form D of regadenoson) including such solid forms as tablets, gelcaps, capsules, caplets, granules, lozenges and bulk powders. The regadenoson can be administered alone or combined with various pharmaceutically acceptable carriers, diluents (such as sucrose, mannitol, lactose, and starches) and excipients known in the art, including, but not limited, to suspending agents, solubilizers, buffering agents, binders, disintegrants, preservatives, colorants, flavorants, lubricants and the like. Time release capsules, tablets and gels are also advantageous in administering the compounds of the present invention.

Suppositories for rectal administration of the regadenoson (such as Form D of regadenoson) can be prepared by mixing the compound with a suitable excipient such as cocoa butter, salicylates and polyethylene glycols. Formulations for vaginal administration can be in the form of a pessary, tampon, cream, gel, past foam, or spray formula containing, in addition to the active ingredient, such suitable carriers as are known in the art.

For topical administration, the pharmaceutical composition can be in the form of creams, ointments, liniments, lotions, emulsions, suspensions, gels, solutions, pastes, powders, sprays, and drops suitable for administration to the skin, eye, ear or nose. Topical administration may also involve transdermal administration via means such as transdermal patches.

Aerosol formulations suitable for administering via inhalation also can be made. For example, for treatment of disorders of the respiratory tract, the compounds according to the invention can be administered by inhalation in the form of a powder (e.g., micronized) or in the form of atomized solutions or suspensions. The aerosol formulation can be placed into a pressurized acceptable propellant.

Methods of Treatment

The present invention further provides methods for treating a condition which requires modulation of an adenosine receptor, e.g., an $A_{2A}$ receptor. The methods involve administering a therapeutically effective amount of (i) regadenoson of the present invention (e.g., Form D of regadenoson, or regadenoson made by a process of the present invention) or (ii) a regadenoson formulation (such as a parenteral solution) prepared from regadenoson of the present invention, to a patient in need thereof. One embodiment is a method of stimulating coronary vasodilation, producing coronary vasodilation.

In additional embodiments, the present invention provides methods of myocardial perfusion imaging that involve administering (i) regadenoson of the present invention or (ii) a regadenoson formulation (such as a parenteral solution) prepared from regadenoson of the present invention, and a radionuclide.

In some embodiments, the compound or composition of the present invention is administered as a mono-therapy. In other embodiments, the compound or composition of the present invention is administered as part of a combination therapy. For example, a compound or composition of the present invention may be used in combination with other drugs or therapies that are used in the treatment/prevention/suppression or amelioration of the diseases or conditions for which compounds and compositions of the present invention are useful.

In certain embodiments, regadenoson of the present invention is administered (or used to prepare a formulation such as a parenteral solution) in an amount of about 0.05 mg, about 0.1 mg, about 0.2 mg, about 0.3 mg, about 0.4 mg, about 0.5 mg, about 1 mg, about 1.5 mg, about 2 mg, about 2.5 mg, about 3 mg, about 3.5 mg, about 4 mg, about 4.5 mg, about 5 mg, about 5.5 mg, about 6 mg, about 6.5 mg, about 7 mg, about 7.5 mg, about 8 mg, about 8.5 mg, about 9 mg, about 9.5 mg or about 10 mg. For example, the active ingredient is administered in an amount of about 0.4 mg, e.g., as an injection containing 0.4 mg regadenoson of the present invention (such as Form D) per 5 mL solution (such as saline) (0.08 mg/mL). In additional embodiments, the amount administered is sufficient to stress the heart and induce a coronary steal situation. In additional embodiments, the amount administered is sufficient for imaging heart or coronary activity in the patient.

Definitions

An "effective amount" refers to the amount of a compound of the present invention that, when administered to a patient (e.g., a mammal) for treating a disorder, is sufficient to effect such treatment for the disorder, or an amount of a compound that is sufficient for modulating a adenosine receptor (e.g., $A_{2A}$ receptor) to achieve the objectives of the invention. The "effective amount" will vary depending on the compound, the disease and its severity and the age, weight, etc., of the patient to be treated.

A subject or patient in whom administration of the therapeutic compound is an effective therapeutic regimen for a disease or disorder is preferably a human, but can be any animal, including a laboratory animal in the context of a clinical trial or screening or activity experiment. Thus, as can be readily appreciated by one of ordinary skill in the art, the methods, compounds and compositions of the present invention are particularly suited to administration to any animal, particularly a mammal, and including, but by no means limited to, humans, domestic animals, such as feline or canine subjects, farm animals, such as but not limited to bovine, equine, caprine, ovine, and porcine subjects, wild animals (whether in the wild or in a zoological garden), research animals, such as mice, rats, rabbits, goats, sheep, pigs, dogs, cats, and avian species, such as chickens, turkeys, and songbirds, i.e., for veterinary medical use.

The following examples are merely illustrative of the present invention and should not be construed as limiting the scope of the invention in any way as many variations and equivalents that are encompassed by the present invention will become apparent to those skilled in the art upon reading the present disclosure.

EXAMPLES

2-Fluoroadenosine and ethyl pyrazole-4-carboxylate are available from Sigma-Aldrich (St. Louis, Mo.). Chelex 100 resin is available from Bio-Rad Laboratories (Hercules, Calif.). The HPLC method for the preparation of N-methyl-4-carboxamide and regadenoson was carried out on an Altima C18 column, 5μ, 4.6 mm×250 mm, using a gradient of 2-70% over 15 min of Buffer B (Buffer A=0.1% triethylamine/0.1% Acetic Acid/3% acetonitrile by volume in DI water, pH ~4.5; Buffer B=10% Buffer A in acetonitrile). The purification of crude regadenoson was carried out on a reverse phase resin using a gradient of 0-70% methanol/water.

X-Ray Powder Diffractions analysis was performed using a Rigaku Ultima IV X-ray diffractometer. The x-ray generator employed a Cu tube operated at 40 kV. The experimental conditions were as follows: Bragg-Brentano focusing method geometry; Incident and receiving Soller slits=5 degrees; divergent and scattered slits=2/3 degree; divergent height limiting slit=10 mm; receiving slit=0.3 mm; scan speed=0.2 degrees/minute; sampling width=0.02 degree; scintillation detector with monochromator.

Example 1

Synthesis of N-Methyl-4-carboxamide 20 g (143 mmol, 1 equiv) of ethyl pyrazole-4-carboxylate and 200 mL (2310 mmol, 16.2 equiv) of a 40% aqueous solution of methylamine were added to a three-necked flask equipped with a condenser and a heating mantle. The mixture was stirred to aid dissolution, and heated to 65° C. for 2 hours. The reaction was monitored using HPLC at 220 nm with a C18 column. The reaction mixture was then concentrated in vacuo to obtain a syrup/solid. The crude product was co-evaporated with acetonitrile (3×200 mL). 100 mL of acetonitrile was then added to the solids and the mixture was stirred for several hours until the solids were well suspended. The solids were then isolated by filtration, washed with 100 mL acetonitrile, and dried in an oven at 40° C. to afford 14.4 g (80% yield) of N-methyl-4-carboxamide with a purity of 93.5% by HPLC.

Example 2

Synthesis of IDAAR-Cu$^{+2}$

This preparation has reported in the literature. See, e.g., Chinese Chemical Letters, (21(1), 51-54, 2010.

An Erlenmeyer flask was charged with 350 mL of water and 75 g of Chelex 100 resin. With stirring, an aqueous solution of copper sulfate pentahydrate (59 g in 350 mL of water) was slowly added over a period of 15 minutes. The resulting slurry was stirred for 2 hours, then filtered. The resulting solids were washed with 100-200 mL of water and dried in a vacuum oven at 50° C. for 16 hours to afford 18 g of IDAAR-Cu$^{+2}$. The copper content of the product was determined to be 11 wt % using Inductively Coupled Plasma Optical Emission Spectroscopy (ICP-OES).

Example 3

Synthesis of Regadenoson Monohydrate 5 g (17.5 mmol, 1 equiv) of 2-fluoroadenosine, 3.07 g (24.5 mmol, 1.4 equiv) of N-methylpyrazole-4-carboxamide, and 32 mL of dimethylsulfoxide were added under a nitrogen atmosphere to a dry 3-necked reaction flask equipped with a condenser and a heating mantle. The mixture was stirred to afford a solution. 100 mL of acetonitrile was then added followed by the addition of 2.2 g of IDAAR-Cu$^{2+}$ and 5.34 g (5.24 mL, 35.1 mmol, 2 equiv) of diazabicycloundecene (DBU). The reaction mixture was heated to 70-80° C. overnight and monitored by HPLC at 260 nm with a C18 column until the reaction was complete. Then, the reaction mixture was evaporated in vacuo to remove most of the acetonitrile. The remaining dimethylsufoxide solution was purified by reverse phase chromatography using methanol and water. The product was dried in vacuo at a temperature that did not exceed 40° C. to afford 3 g (44% yield) of regadenoson monohydrate.

Example 4

Synthesis of 2-Hydazineadenosine 2-fluoroadenosine (4 g, 14 mmol) was dissolved in 100 mL ethanol in a 300 mL three-necked flask. Hydrazine hydrate (4.1 mL, 6 equivalents, 84 mmol) was added and the mixture was heated to reflux for 1 hour. The reaction mixture was allowed to cool to room temperature and stirred overnight (16 hours). The resulting white precipitate was isolated by filtration and dried in oven at 40° C. overnight to afford 2-hydrazinoadenosine (yield: 94%, 3.5 g, 96% purity).

Example 5

Synthesis of Regadenoson Form D

2-Fluoroadenosine (45 g, 0.158 mol., 1 eq.), 4-(N-methyl-carboxamido)pyrazole (27.64 g, 0.221 mol., 1.4 eq.), dimethylsulfoxide (DMSO) (320 mL) and acetonitrile (960 mL) were added to a dry 3000 ml 3-neck reaction flask equipped with a condenser and heating mantle. After stirring for 10 minutes, IDAAR-Cu (20.07 g, 0.032 mol., 0.2 eq.) and DBU (48.0 g, 0.316 mol., 2 eq.) were added. The resulting mixture was then heated to 65° C. overnight (18 hours).

The reaction mixture was then filtered and the filtrate was evaporated followed by 2×500 mL co-evaporation with xylene. The residue was diluted with 5 L acetonitrile, transferred to a 10 L flask and kept in a cold room (4° C.) overnight. The resulting white precipitate was isolated by filtration and stirred in 1.8 L of water. The mixture was heated to 80° C. for 2 hours, then allowed to cool in a cold room (4° C.) overnight.

The white precipitate was isolated by filtration, then dissolved in 200 ml of 1:1 mixture of DMSO and methanol. The clear and slightly yellow solution was loaded to a reverse phase column (10 L) and eluted with water/methanol (gradient with a 5% increase of MeOH every 10 L).

The fractions with HPLC purity of more than 99.9% were combined and concentrated to a paste. The supernatant liquid was decanted and the flask heated in an oil-bath at 150° C. under reduced pressure of 20 mmHg for 6 hours to afford 6.2 g of Regadenoson Form D as white solid (99.94% HPLC, KF analysis 0.8%).

The fractions with HPLC purity between 50 and 99.8% (~23 g of product as indicated by HPLC) were combined and subjected to a second purification stage.

The present invention is not to be limited in scope by the specific embodiments described herein. Indeed, various modifications of the invention in addition to those described herein will become apparent to those skilled in the art from the foregoing description and the accompanying figures.

Such modifications are intended to fall within the scope of the appended claims. Patents, patent applications, publications, product descriptions, and protocols are cited throughout this application, the disclosures of which are incorporated herein by reference in their entireties for all purposes.

What is claimed is:

1. A process for the preparation of regadenoson of Formula (IA), a pharmaceutically acceptable salt thereof, or a hydrate thereof:

comprising contacting 2-fluoroadenosine of Formula (IIA) with 4-N-methylcarboxamide pyrazole of Formula (IIIA):

in the presence of a metal catalyst and a base.

2. The process of claim 1, wherein the reaction is conducted in a solvent selected from acetonitrile, dimethylsulfoxide, and mixtures thereof.

3. The process of claim 1, wherein the base is selected from sodium hydroxide, potassium hydroxide, 1,8-diazabicyclo[5.4.0]undec-7-ene (DBU), 1,4-diazabicyclo[2.2.2]octane (DABCO), and combinations thereof.

4. The process of claim 3, wherein the base is DBU.

5. The process of claim 1, wherein the metal catalyst is a copper (II) catalyst.

6. The process of claim 5, wherein the copper (II) catalyst is chelated to a resin.

7. The process of claim 1, wherein the reaction is conducted at a temperature of between about 60° C. and about 90° C.

8. The process of claim 1, wherein the regadenoson of Formula (IA) is a monohydrate.

9. The process of claim 1, further comprising converting the regadenoson, or hydrate thereof, to a pharmaceutically acceptable salt thereof.

10. The process of claim 1, further comprising the step of subjecting the regadenoson to reverse phase chromatography.

11. The process of claim 10, wherein the column is eluted with water and methanol.

12. A composition comprising:
(a) regadenoson, and
(b) 2-fluoroadenosine of Formula (IIA)

in an amount up to about 0.2%, based upon the total weight of the composition.

13. A parenteral solution comprising the composition of claim 12.

14. A crystalline form of regadenoson (Form D) having an X-Ray powder diffraction pattern substantially as shown in FIG. 4.

15. The crystalline form of regadenoson (Form D) of claim 14, wherein the crystalline form contains between about 0.8 and about 1.7% by weight of water of hydration.

16. A pharmaceutical composition comprising a crystalline form of claim 14 and a pharmaceutically acceptable carrier.

17. A method of preparing a parenteral solution of regadenoson comprising dissolving Form D of regadenoson of claim 14 in an aqueous solution and optionally adding one or more pharmaceutically acceptable excipients.

* * * * *